(12) United States Patent
Dempsey et al.

(10) Patent No.: US 11,612,764 B2
(45) Date of Patent: *Mar. 28, 2023

(54) SYSTEMS AND METHODS FOR LINEAR ACCELERATOR RADIOTHERAPY WITH MAGNETIC RESONANCE IMAGING

(71) Applicant: ViewRay Technologies, Inc., Oakwood Village, OH (US)

(72) Inventors: James F. Dempsey, Atherton, CA (US); Shmaryu M. Shvartsman, Highland Heights, OH (US)

(73) Assignee: VIEWRAY TECHNOLOGIES, INC., Oakwood Village, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/397,214

(22) Filed: Aug. 9, 2021

(65) Prior Publication Data

US 2021/0361973 A1 Nov. 25, 2021

Related U.S. Application Data

(63) Continuation of application No. 16/598,564, filed on Oct. 10, 2019, now Pat. No. 11,083,912, which is a
(Continued)

(51) Int. Cl.
*A61N 5/10* (2006.01)
*G01R 33/422* (2006.01)
(Continued)

(52) U.S. Cl.
CPC ....... *A61N 5/1049* (2013.01); *G01R 33/3607* (2013.01); *G01R 33/421* (2013.01);
(Continued)

(58) Field of Classification Search
CPC .......... A61N 5/1049; A61N 2005/1055; A61N 2005/1094; G01R 33/3607; G01R 33/421;
(Continued)

(56) References Cited

U.S. PATENT DOCUMENTS

| 3,569,823 A | 3/1971 | Golay |
| 3,735,306 A | 5/1973 | Kabler |

(Continued)

FOREIGN PATENT DOCUMENTS

| CN | 1394550 A | 2/2003 |
| CN | 1946339 A | 4/2007 |

(Continued)

OTHER PUBLICATIONS

AU App. No. 2017200361; Notice of Acceptance dated Oct. 30, 2018 (pp. 1-3).
(Continued)

*Primary Examiner* — Dixomara Vargas
(74) *Attorney, Agent, or Firm* — Pillsbury Winthrop Shaw Pittman LLP

(57) ABSTRACT

Systems and methods for the delivery of linear accelerator radiotherapy in conjunction with magnetic resonance imaging in which components of a linear accelerator may be placed in shielding containers around a gantry, may be connected with RF waveguides, and may employ various systems and methods for magnetic and radio frequency shielding.

16 Claims, 5 Drawing Sheets

Related U.S. Application Data continuation of application No. 15/268,366, filed on Sep. 16, 2016, now Pat. No. 10,463,884, which is a continuation of application No. 13/841,478, filed on Mar. 15, 2013, now Pat. No. 9,446,263.

(51) Int. Cl.
  *G01R 33/48* (2006.01)
  *G01R 33/36* (2006.01)
  *G01R 33/421* (2006.01)
  *G01R 33/38* (2006.01)

(52) U.S. Cl.
  CPC ....... *G01R 33/422* (2013.01); *G01R 33/4808* (2013.01); *A61N 2005/1055* (2013.01); *A61N 2005/1094* (2013.01); *G01R 33/3806* (2013.01); *Y10T 29/49018* (2015.01)

(58) Field of Classification Search
  CPC .............. G01R 33/422; G01R 33/4808; G01R 33/3806
  See application file for complete search history.

(56) References Cited

U.S. PATENT DOCUMENTS

| | | |
|---|---|---|
| 4,642,569 A | 2/1987 | Hayes |
| 4,652,826 A | 3/1987 | Yamamoto |
| 4,694,837 A | 9/1987 | Blakeley |
| 4,740,753 A | 4/1988 | Glover |
| 5,006,804 A | 4/1991 | Dorri |
| 5,216,255 A | 6/1993 | Weidlich |
| 5,280,428 A | 1/1994 | Wu |
| 5,295,488 A | 3/1994 | Lloyd |
| 5,317,616 A | 5/1994 | Swerdloff |
| 5,331,552 A | 7/1994 | Lloyd |
| 5,332,908 A | 7/1994 | Weidlich |
| 5,351,280 A | 9/1994 | Swerdloff |
| 5,361,763 A | 11/1994 | Kao |
| 5,365,927 A | 11/1994 | Roemer |
| 5,373,239 A | 12/1994 | Marek |
| 5,373,844 A | 12/1994 | Smith |
| 5,378,989 A | 1/1995 | Barber |
| 5,442,675 A | 8/1995 | Swerdloff |
| 5,458,125 A | 10/1995 | Schweikard |
| 5,513,238 A | 4/1996 | Leber |
| 5,530,352 A | 6/1996 | Kolem |
| 5,537,452 A | 7/1996 | Shepherd |
| 5,538,494 A | 7/1996 | Matsuda |
| 5,555,283 A | 9/1996 | Shiu |
| 5,585,724 A | 12/1996 | Morich |
| 5,592,091 A | 1/1997 | Manabe |
| 5,596,619 A | 1/1997 | Carol |
| 5,602,892 A | 2/1997 | Llacer |
| 5,602,982 A | 2/1997 | Llacer |
| 5,659,281 A | 8/1997 | Pissanetzky |
| 5,675,305 A | 10/1997 | Demeester |
| 5,724,400 A | 3/1998 | Swerdloff |
| 5,734,384 A | 3/1998 | Yanof |
| 5,740,225 A | 4/1998 | Nabatame |
| 5,748,700 A | 5/1998 | Shepherd |
| 5,751,781 A | 5/1998 | Brown |
| 5,757,881 A | 5/1998 | Hughes |
| 5,760,582 A | 6/1998 | Morrone |
| 5,802,136 A | 9/1998 | Carol |
| 5,815,547 A | 9/1998 | Shepherd |
| 5,851,182 A | 12/1998 | Sahadevan |
| 5,894,503 A | 4/1999 | Shepherd |
| 5,952,830 A | 9/1999 | Petropoulos |
| 6,005,916 A | 12/1999 | Johnson |
| 6,038,283 A | 3/2000 | Carol |
| 6,052,430 A | 4/2000 | Siochi |
| 6,104,779 A | 8/2000 | Shepherd |
| 6,112,112 A | 8/2000 | Gilhuijs |
| 6,144,875 A | 11/2000 | Schweikard |
| 6,157,278 A | 12/2000 | Katznelson |
| 6,175,761 B1 | 1/2001 | Frandsen |
| 6,198,957 B1 | 3/2001 | Green |
| 6,223,067 B1 | 4/2001 | Vilsmeier |
| 6,240,162 B1 | 5/2001 | Hernandez-Guerra |
| 6,260,005 B1 | 7/2001 | Yang |
| 6,311,389 B1 | 11/2001 | Uosaki |
| 6,314,159 B1 | 11/2001 | Siochi |
| 6,330,300 B1 | 12/2001 | Siochi |
| 6,349,129 B1 | 2/2002 | Siochi |
| 6,366,798 B2 | 4/2002 | Green |
| 6,381,486 B1 | 4/2002 | Mistretta |
| 6,385,286 B1 | 5/2002 | Fitchard |
| 6,385,477 B1 | 5/2002 | Werner |
| 6,393,096 B1 | 5/2002 | Carol |
| 6,411,675 B1 | 6/2002 | Llacer |
| 6,414,487 B1 | 7/2002 | Anand |
| 6,422,748 B1 | 7/2002 | Shepherd |
| 6,424,856 B1 | 7/2002 | Vilsmeier |
| 6,466,813 B1 | 10/2002 | Shukla |
| 6,487,435 B2 | 11/2002 | Mistretta |
| 6,504,899 B2 | 1/2003 | Pugachev |
| 6,509,735 B2 | 1/2003 | Mueller |
| 6,512,813 B1 | 1/2003 | Krispel |
| 6,516,046 B1 | 2/2003 | Frohlich |
| 6,526,123 B2 | 2/2003 | Ein-Gal |
| 6,527,443 B1 | 3/2003 | Vilsmeier |
| 6,542,767 B1 | 4/2003 | McNichols |
| 6,546,073 B1 | 4/2003 | Lee |
| 6,560,311 B1 | 5/2003 | Shepard |
| 6,564,084 B2 | 5/2003 | Allred |
| 6,570,475 B1 | 5/2003 | Lvovsky |
| 6,584,174 B2 | 6/2003 | Schubert |
| 6,591,127 B1 | 7/2003 | McKinnon |
| 6,594,516 B1 | 7/2003 | Steckner |
| 6,600,810 B1 | 7/2003 | Hughes |
| 6,609,022 B2 | 8/2003 | Vilsmeier |
| 6,611,700 B1 | 8/2003 | Vilsmeier |
| 6,618,467 B1 | 9/2003 | Ruchala |
| 6,636,645 B1 | 10/2003 | Yu |
| 6,657,391 B2 | 12/2003 | Ding |
| 6,661,870 B2 | 12/2003 | Kapatoes |
| 6,708,054 B2 | 3/2004 | Shukla |
| 6,719,683 B2 | 4/2004 | Frohlich |
| 6,724,922 B1 | 4/2004 | Vilsmeier |
| 6,728,336 B2 | 4/2004 | Bortfeld |
| 6,731,970 B2 | 5/2004 | Schlossbauer |
| 6,735,277 B2 | 5/2004 | McNutt |
| 6,757,355 B1 | 6/2004 | Siochi |
| 6,772,002 B2 | 8/2004 | Schmidt |
| 6,778,850 B1 | 8/2004 | Adler |
| 6,788,060 B1 | 9/2004 | Feenan |
| 6,792,074 B2 | 9/2004 | Erbel |
| 6,806,712 B2 | 10/2004 | Akgun |
| 6,849,129 B2 | 2/2005 | Bilz et al. |
| 6,853,704 B2 | 2/2005 | Collins |
| 6,859,660 B2 | 2/2005 | Vilsmeier |
| 6,862,469 B2 | 3/2005 | Bucholz |
| 6,865,253 B2 | 3/2005 | Blumhofer |
| 6,865,411 B2 | 3/2005 | Erbel |
| 6,879,714 B2 | 4/2005 | Hutter |
| 6,885,886 B2 | 4/2005 | Bauch |
| 6,891,375 B2 | 5/2005 | Goto |
| 6,898,456 B2 | 5/2005 | Erbel |
| 6,915,005 B1 | 7/2005 | Ruchala |
| 6,937,696 B1 | 8/2005 | Mostafavi |
| 6,940,281 B2 | 9/2005 | Feenan |
| 6,947,582 B1 | 9/2005 | Vilsmeier |
| 6,965,847 B2 | 11/2005 | Wessol |
| 6,980,679 B2 | 12/2005 | Jeung |
| 6,999,555 B2 | 2/2006 | Morf |
| 7,012,385 B1 | 3/2006 | Kulish |
| 7,046,762 B2 | 5/2006 | Lee |
| 7,046,765 B2 | 5/2006 | Wong |
| 7,046,831 B2 | 5/2006 | Ruchala |
| 7,050,845 B2 | 5/2006 | Vilsmeier |
| 7,092,573 B2 | 8/2006 | Luo |
| 7,095,823 B2 | 8/2006 | Topolnjak |
| 7,096,055 B1 | 8/2006 | Schweikard |

(56) References Cited

U.S. PATENT DOCUMENTS

| | | | |
|---|---|---|---|
| 7,123,758 B2 | 10/2006 | Jeung | |
| 7,130,372 B2 | 10/2006 | Kusch | |
| 7,154,991 B2 | 12/2006 | Earnst | |
| 7,162,005 B2 | 1/2007 | Bjorkholm | |
| 7,166,852 B2 | 1/2007 | Saracen | |
| 7,171,257 B2 | 1/2007 | Thomson | |
| 7,180,366 B2 | 2/2007 | Roos | |
| 7,191,100 B2 | 3/2007 | Mostafavi | |
| 7,202,663 B2 | 4/2007 | Huang | |
| 7,204,640 B2 | 4/2007 | Fu | |
| 7,221,733 B1 | 5/2007 | Takai | |
| 7,227,925 B1 | 6/2007 | Mansfield | |
| 7,230,429 B1 | 6/2007 | Huang | |
| 7,231,075 B2 | 6/2007 | Raghavan | |
| 7,231,076 B2 | 6/2007 | Fu | |
| 7,260,426 B2 | 8/2007 | Schweikard | |
| 7,265,545 B2 | 9/2007 | Krueger | |
| 7,266,175 B1 | 9/2007 | Romesberg | |
| 7,266,176 B2 | 9/2007 | Allison | |
| 7,289,599 B2 | 10/2007 | Seppi | |
| 7,298,819 B2 | 11/2007 | Dooley | |
| 7,302,038 B2 | 11/2007 | Mackie | |
| 7,315,636 B2 | 1/2008 | Kuduvalli | |
| 7,317,782 B2 | 1/2008 | Bjorkholm | |
| 7,318,805 B2 | 1/2008 | Schweikard | |
| 7,324,626 B2 | 1/2008 | Vilsmeier | |
| 7,327,865 B2 | 2/2008 | Fu | |
| 7,366,278 B2 | 4/2008 | Fu | |
| 7,394,081 B2 | 7/2008 | Okazaki | |
| 7,403,638 B2 | 7/2008 | Jeung | |
| 7,412,029 B2 | 8/2008 | Myles | |
| 7,415,095 B2 | 8/2008 | Wofford | |
| 7,423,273 B2 | 9/2008 | Clayton | |
| 7,426,318 B2 | 9/2008 | Fu | |
| 7,444,178 B2 | 10/2008 | Goldbach | |
| 7,453,264 B2 | 11/2008 | Trequattrini | |
| 7,463,823 B2 | 12/2008 | Birkenbach | |
| 7,471,813 B2 | 12/2008 | Ulmer | |
| 7,477,776 B2 | 1/2009 | Lachner | |
| 7,480,399 B2 | 1/2009 | Fu | |
| 7,489,131 B2 | 2/2009 | Lvovsky | |
| 7,505,037 B2 | 3/2009 | Wang | |
| 7,505,617 B2 | 3/2009 | Fu | |
| 7,522,779 B2 | 4/2009 | Fu | |
| 7,532,705 B2 | 5/2009 | Yin | |
| 7,535,229 B2 | 5/2009 | Schlueter | |
| 7,542,622 B1 | 6/2009 | Angelini | |
| 7,558,617 B2 | 7/2009 | Vilsmeier | |
| 7,570,987 B2 | 8/2009 | Raabe | |
| 7,577,474 B2 | 8/2009 | Vilsmeier | |
| 7,589,326 B2 | 9/2009 | Mollov | |
| 7,634,122 B2 | 12/2009 | Bertram | |
| 7,636,417 B2 | 12/2009 | Bjorkholm | |
| 7,638,752 B2 | 12/2009 | Partain | |
| 7,657,304 B2 | 2/2010 | Mansfield | |
| 7,659,718 B1 | 2/2010 | Lustig | |
| 7,688,998 B2 | 3/2010 | Tuma | |
| 7,728,311 B2 | 6/2010 | Gall | |
| 7,741,624 B1 | 6/2010 | Sahadevan | |
| 7,785,358 B2 | 8/2010 | Lach | |
| 7,791,338 B2 | 9/2010 | Kim | |
| 7,840,045 B2 | 11/2010 | Guo | |
| 7,902,530 B1 | 3/2011 | Sahadevan | |
| 7,907,987 B2 | 3/2011 | Dempsey | |
| 7,957,507 B2 | 6/2011 | Cadman | |
| 8,139,714 B1 | 3/2012 | Sahadevan | |
| 8,155,417 B2 | 4/2012 | Piron | |
| 8,173,983 B1 | 5/2012 | Sahadevan | |
| 8,190,233 B2 | 5/2012 | Dempsey | |
| 8,214,010 B2 | 7/2012 | Courtney | |
| 8,310,233 B2 | 11/2012 | Trzasko | |
| 8,331,531 B2 | 12/2012 | Fahrig | |
| 8,334,697 B2 | 12/2012 | Overweg | |
| 8,378,677 B2 | 2/2013 | Morich | |
| 8,460,195 B2 | 6/2013 | Courtney | |
| 8,570,042 B2 | 10/2013 | Pines | |
| 8,803,524 B2 | 8/2014 | Dempsey | |
| 8,836,332 B2 | 9/2014 | Shvartsman | |
| 8,896,308 B2 | 11/2014 | Shvartsman | |
| 8,981,779 B2 | 3/2015 | Shvartsman | |
| 8,983,573 B2 | 3/2015 | Carlone | |
| 9,114,253 B2 | 8/2015 | Dempsey | |
| 9,289,626 B2 | 3/2016 | Kawrakow | |
| 9,421,398 B2 | 8/2016 | Shvartsman | |
| 9,423,477 B2 | 8/2016 | Dempsey | |
| 9,446,263 B2 * | 9/2016 | Dempsey | G01R 33/3607 |
| 9,472,000 B2 | 10/2016 | Dempsey | |
| 9,498,167 B2 | 11/2016 | Mostafavi | |
| 9,526,918 B2 | 12/2016 | Kruip | |
| 9,675,271 B2 | 6/2017 | Shvartsman | |
| 2001/0001807 A1 * | 5/2001 | Green | A61N 5/1042 378/65 |
| 2001/0049475 A1 | 12/2001 | Bucholz | |
| 2002/0046010 A1 | 4/2002 | Wessol | |
| 2002/0091315 A1 | 7/2002 | Spetz | |
| 2002/0150207 A1 | 10/2002 | Kapatoes | |
| 2003/0068097 A1 | 4/2003 | Wilson | |
| 2003/0094947 A1 | 5/2003 | Akgun | |
| 2003/0112107 A1 | 6/2003 | Forbes | |
| 2003/0155530 A1 | 8/2003 | Adnani | |
| 2003/0181804 A1 | 9/2003 | Gagnon | |
| 2003/0197507 A1 | 10/2003 | Liu | |
| 2003/0219098 A1 | 11/2003 | McNutt | |
| 2004/0054248 A1 | 3/2004 | Kimchy | |
| 2004/0239327 A1 | 12/2004 | Heid | |
| 2004/0254448 A1 | 12/2004 | Amies | |
| 2004/0254773 A1 | 12/2004 | Zhang | |
| 2005/0030028 A1 | 2/2005 | Clarke | |
| 2005/0053267 A1 | 3/2005 | Mostafavi | |
| 2005/0054916 A1 | 3/2005 | Mostafavi | |
| 2005/0077899 A1 | 4/2005 | Jacobs | |
| 2005/0143965 A1 | 6/2005 | Failla | |
| 2005/0197564 A1 | 9/2005 | Dempsey | |
| 2005/0197654 A1 | 9/2005 | Edman | |
| 2005/0201516 A1 | 9/2005 | Ruchala | |
| 2005/0207531 A1 | 9/2005 | Dempsey | |
| 2005/0254623 A1 | 11/2005 | Kamath | |
| 2006/0033496 A1 | 2/2006 | Shvartsman | |
| 2006/0058636 A1 | 3/2006 | Wemple | |
| 2006/0074292 A1 | 4/2006 | Thomson | |
| 2006/0120583 A1 | 6/2006 | Dewaele | |
| 2006/0193441 A1 | 8/2006 | Cadman | |
| 2007/0003021 A1 | 1/2007 | Guertin | |
| 2007/0016014 A1 | 1/2007 | Hara | |
| 2007/0052420 A1 | 3/2007 | Speck | |
| 2007/0053492 A1 | 3/2007 | Kidani | |
| 2007/0083114 A1 | 4/2007 | Yang | |
| 2007/0086569 A1 | 4/2007 | Johnsen | |
| 2007/0197908 A1 | 8/2007 | Ruchala | |
| 2007/0230770 A1 | 10/2007 | Kulkarni | |
| 2007/0244386 A1 | 10/2007 | Steckner | |
| 2008/0024130 A1 | 1/2008 | Schlueter | |
| 2008/0049896 A1 * | 2/2008 | Kuduvalli | A61N 5/1049 378/65 |
| 2008/0049897 A1 | 2/2008 | Molloy | |
| 2008/0093567 A1 | 4/2008 | Gall | |
| 2008/0116894 A1 | 5/2008 | Weiger | |
| 2008/0177138 A1 | 7/2008 | Courtney | |
| 2008/0197842 A1 | 8/2008 | Lustig | |
| 2008/0208036 A1 | 8/2008 | Amies | |
| 2008/0303457 A1 | 12/2008 | Maltz | |
| 2009/0039886 A1 | 2/2009 | White | |
| 2009/0060130 A1 | 3/2009 | Wilkens | |
| 2009/0129545 A1 | 5/2009 | Adler | |
| 2009/0147916 A1 | 6/2009 | Fallone | |
| 2009/0149735 A1 | 6/2009 | Fallone | |
| 2009/0175418 A1 | 7/2009 | Sakurai | |
| 2009/0264768 A1 | 10/2009 | Courtney | |
| 2010/0033186 A1 | 2/2010 | Overweg | |
| 2010/0049030 A1 | 2/2010 | Saunders | |
| 2010/0113911 A1 | 5/2010 | Dempsey | |
| 2010/0239066 A1 | 9/2010 | Fahrig | |
| 2010/0312100 A1 | 12/2010 | Zarkh | |
| 2010/0322497 A1 | 12/2010 | Dempsey | |

(56) References Cited

U.S. PATENT DOCUMENTS

| | | |
|---|---|---|
| 2011/0012593 A1* | 1/2011 | Shvartsman ......... G01R 33/421 324/307 |
| 2011/0051893 A1 | 3/2011 | Mcnutt |
| 2011/0118588 A1 | 5/2011 | Kornblau |
| 2011/0121832 A1 | 5/2011 | Shvartsman |
| 2011/0150180 A1 | 6/2011 | Balakin |
| 2011/0204262 A1 | 8/2011 | Pu |
| 2011/0218420 A1 | 9/2011 | Carlone |
| 2011/0237859 A1 | 9/2011 | Kuhn |
| 2011/0241684 A1 | 10/2011 | Dempsey |
| 2011/0284757 A1 | 11/2011 | Butuceanu |
| 2011/0304416 A1 | 12/2011 | Warner |
| 2012/0019246 A1 | 1/2012 | Kannengiesser |
| 2012/0022363 A1 | 1/2012 | Dempsey |
| 2012/0150017 A1 | 6/2012 | Yamaya |
| 2012/0165652 A1 | 6/2012 | Dempsey |
| 2012/0230462 A1 | 9/2012 | Robar |
| 2012/0245453 A1 | 9/2012 | Tryggestad |
| 2012/0253172 A1 | 10/2012 | Loeffler |
| 2013/0066135 A1 | 3/2013 | Rosa |
| 2013/0090547 A1 | 4/2013 | Bani-Hashemi |
| 2013/0090549 A1 | 4/2013 | Meltsner |
| 2013/0147476 A1 | 6/2013 | Shvartsman |
| 2013/0225975 A1 | 8/2013 | Harvey |
| 2013/0245425 A1 | 9/2013 | Dempsey |
| 2013/0261429 A1 | 10/2013 | Lee |
| 2013/0261430 A1 | 10/2013 | Uhlemann |
| 2013/0296687 A1 | 11/2013 | Dempsey |
| 2013/0345545 A1 | 12/2013 | Gross |
| 2013/0345556 A1 | 12/2013 | Courtney |
| 2014/0003023 A1 | 1/2014 | Weibler |
| 2014/0010355 A1 | 1/2014 | Seeber |
| 2014/0077098 A1 | 3/2014 | Tachikawa |
| 2014/0084926 A1 | 3/2014 | Amthor |
| 2014/0112453 A1 | 4/2014 | Prince |
| 2014/0121495 A1 | 5/2014 | Dempsey |
| 2014/0128719 A1 | 5/2014 | Longfield |
| 2014/0135615 A1 | 5/2014 | Krulp |
| 2014/0263990 A1 | 9/2014 | Kawrykow |
| 2014/0266206 A1 | 9/2014 | Dempsey |
| 2014/0266208 A1* | 9/2014 | Dempsey ............. A61N 5/1049 29/601 |
| 2014/0275963 A1 | 9/2014 | Shvartsman |
| 2014/0330108 A1 | 11/2014 | Dempsey |
| 2014/0336442 A1 | 11/2014 | Keppel |
| 2014/0347053 A1 | 11/2014 | Dempsey |
| 2015/0065860 A1 | 3/2015 | Shvartsman |
| 2015/0077118 A1 | 3/2015 | Shvartsman |
| 2015/0095044 A1 | 4/2015 | Hartman |
| 2015/0126850 A1 | 5/2015 | Cetingul |
| 2015/0154756 A1 | 6/2015 | Gerganov |
| 2015/0165233 A1 | 6/2015 | Dempsey |
| 2015/0185300 A1 | 7/2015 | Shvartsman |
| 2015/0251020 A1 | 9/2015 | Calone |
| 2015/0346304 A1 | 12/2015 | Hu |
| 2016/0011288 A1 | 1/2016 | Overweg |
| 2016/0067525 A1 | 3/2016 | Bouchet |
| 2016/0232690 A1 | 8/2016 | Ahmad |
| 2016/0252596 A1 | 9/2016 | Nielsen |
| 2016/0256712 A1 | 9/2016 | Vahala |
| 2016/0278719 A1 | 9/2016 | Jensen |
| 2016/0334479 A1 | 11/2016 | Poole |
| 2016/0356869 A1 | 12/2016 | Dempsey |
| 2017/0001039 A1 | 1/2017 | Dempsey |
| 2017/0014644 A1 | 1/2017 | Shvartsman |
| 2017/0021198 A1 | 1/2017 | Kawrykow |
| 2017/0120075 A1 | 5/2017 | Overweg |
| 2017/0176556 A1 | 6/2017 | Shvartsman |
| 2017/0231583 A1 | 8/2017 | Goteti Venkata |
| 2017/0252577 A1 | 9/2017 | Dempsey |
| 2017/0371001 A1 | 12/2017 | Dempsey |
| 2018/0003789 A1 | 1/2018 | Amthor |
| 2018/0021595 A1 | 1/2018 | Kesti-Helia |
| 2018/0078785 A1 | 3/2018 | Ollila |
| 2018/0078792 A1 | 3/2018 | Ollila |
| 2018/0185669 A1 | 7/2018 | Kuusela |
| 2018/0243584 A1 | 8/2018 | Nord |
| 2019/0004131 A1 | 1/2019 | Wachowicz |
| 2019/0060670 A1 | 2/2019 | Ni |
| 2019/0083814 A1 | 3/2019 | Tallinen |
| 2019/0090777 A1 | 3/2019 | Leghissa |
| 2019/0168028 A1 | 6/2019 | Dempsey |
| 2019/0217126 A1 | 7/2019 | Shvartsman |
| 2019/0353724 A1 | 11/2019 | Snelten |
| 2019/0353725 A1 | 11/2019 | Dempsey |
| 2020/0086143 A1 | 3/2020 | Maltz |
| 2020/0147412 A1 | 5/2020 | Cheng |
| 2020/0246637 A1 | 8/2020 | Wang |

FOREIGN PATENT DOCUMENTS

| | | |
|---|---|---|
| CN | 101309726 A | 11/2008 |
| CN | 101452065 A | 6/2009 |
| CN | 102247658 A | 11/2011 |
| CN | 102472830 A | 5/2012 |
| CN | 102641561 A | 8/2012 |
| CN | 102713682 A | 10/2012 |
| EP | 0152554 A2 | 8/1985 |
| EP | 2230530 A1 | 9/2010 |
| EP | 2359905 A1 | 8/2011 |
| FR | 2839894 A1 | 11/2003 |
| GB | 2393373 A | 3/2004 |
| JP | H03243877 A | 10/1991 |
| JP | H07148142 A | 6/1995 |
| JP | H07213507 A | 8/1995 |
| JP | 2001517132 A | 10/2001 |
| JP | 2002186676 A | 7/2002 |
| JP | 2002522129 A | 7/2002 |
| JP | 2004351207 A | 12/2004 |
| JP | 2005103295 A | 4/2005 |
| JP | 2007526036 A | 9/2007 |
| JP | 2008194449 | 8/2008 |
| JP | 2008532681 | 8/2008 |
| JP | 2009501043 A | 1/2009 |
| JP | 2009511222 A | 3/2009 |
| JP | 2009112870 A | 5/2009 |
| JP | 2009160309 A | 7/2009 |
| JP | 6224020 | 7/2015 |
| WO | 1993018707 | 9/1993 |
| WO | 1999032189 | 7/1999 |
| WO | 2002072190 A2 | 9/2002 |
| WO | 20030008986 | 1/2003 |
| WO | 2004024235 A1 | 3/2004 |
| WO | 2005081842 A2 | 9/2005 |
| WO | 2006007277 A2 | 1/2006 |
| WO | 2006097274 A1 | 9/2006 |
| WO | 2006097864 A1 | 9/2006 |
| WO | 2007007276 A2 | 1/2007 |
| WO | 2007012933 A2 | 2/2007 |
| WO | 2007045076 A1 | 4/2007 |
| WO | 2008013598 A2 | 1/2008 |
| WO | 2008122899 A1 | 10/2008 |
| WO | 2009004521 A2 | 1/2009 |
| WO | 2009107005 A2 | 9/2009 |
| WO | 2009155700 A1 | 12/2009 |
| WO | 2010103644 A1 | 9/2010 |
| WO | 2011008969 A1 | 1/2011 |
| WO | 2011063342 A1 | 5/2011 |
| WO | 2012164527 A1 | 12/2012 |
| WO | 2015085008 A1 | 6/2015 |
| WO | 20150138945 | 9/2015 |

OTHER PUBLICATIONS

AU Search Report dated Dec. 11, 2017.
B W Raaymakers et al.; "Integrating a 1.5 T MRI Scanner with a 6 MV Accelerator: Proof of Concepts," Physics in Medicine and Biology. vol. 54, No. 12, May 19, 2009, pp. N229-N237, XP055395399, Bristol GB ISSN: 0031-9155. 9 pages.
Balter, James M., et al. 'Accuracy of a Wireless Localization System for Radiotherapy' Int. J. Radiation Oncology Biol. Phys., vol. 61, No. 3. pp. 933-937, Nov. 1, 2004, Elsevier Inc., USA.

(56) References Cited

OTHER PUBLICATIONS

Baro, J et al. 'Penelope: An algorithm for Monte Carlo simulation of the penetration and energy loss of electrons and positrons in matter' Nuclear Instruments and Methods in Physics Research B 100 (1995) 31-46, received Sep. 30, 1994, Elsevier Science B.V.
Barth, et al. "Simultaneous Multislice (SMS) Imaging Techniques." Magnetic Resonance in Medicine; vol. 75; pp. 63-81; 2016.
Bernier, Jacques et al. 'Radiation oncology: a century of achievements' Nature Reviews-Cancer, vol. 4, Sep. 2004. pp. 737-747.
Bilgin, A. et al. 'Randomly Perturbed Radial Trajectories for Compressed Sensing MRI.' Proceedings of International Society for Magnetic Resonance in Medicine 16 (2008):p. 3152.
Blaimer, et al. 'Smash, Sense, Pills, Grappa, How to Choose the Optimal Method'. Top Magan Reson Imaging, vol. 15, No. 4, Aug. 2004, pp. 223-236.
Buchanan, Roger 'Cobalt on the way out' British Medical Journal, vol. 292, Feb. 1, 1986. p. 290.
Candes, et al. 'Robust Uncertainty Principles: Exact Signal Reconstruction from Highly Incomplete Frequency Information.' IEEE Transactions on Information Theory, vol. 52, No. 2, Feb. 2006, pp. 489-509.
Candes, et al. 'Sparsity and Incoherence in Compressive Sampling'. Electrical and Computer Engineering, Georgia Tech, Atlanta, GA, 90332. Nov. 2006, pp. 1-20.
Chng, N. et al. 'Development of inverse planning and limited angle CT reconstruction for cobalt-60 tomotherapy' Proceedings of 51st Annual Meeting of Canadian Organization of Medical Physicists and the Canadian College of Physicists in Medicine, 2005, McMaster University, Hamilton Ontario. Medical Physics, 2005, p. 2426. (4 pages).
CIPRA 'L1-magic' from SIAM News, vol. 39, No. 9, Nov. 2006. (3 pages).
CN App. No. 201610115787.5; Second Office Action dated Oct. 15, 2018.
Corrected Notice of Allowability dated Mar. 15, 2021 for U.S. Appl. No. 16/204,838 (pp. 1-2).
De Poorter J. et al. 'Noninvasive MRI Thermometry with the Proton Resonance Frequencey (PRF) Method: In Vivo Results in Human Muscle,' Magnetic Resonance in Medicine, Academic Press, Duluth, vol. 33, No. 1, Jan. 1995 pp. 74-81 XP000482971.
Donoho, David L., 'Compressed Sensing'. Department of Statistics, Stanford University. Sep. 14, 2004. (34 pages).
EP App. No. 10195476.6; Extended EP Search Report dated Jul. 4, 2011; 11 pages.
EP App. No. 10800553.9; Extended EP Search Report dated Oct. 17, 2013; 10 pages.
EP App. No. 17000760.3; Extended EP Search Report dated Nov. 9, 2017; 7 pages.
Foroosh, Hassan, et.al. 'Extension of Phase Correlation to Subpixel Registration.' IEEE Transactions on Image Processing, vol. 11, No. 3, 2002, pp. 188-200.
Gerganov G et al, 'Portal image registration using the phase correlation method', 2013 IEEE Nuclear Science Symposium and Medical Imaging Conference (2013 NSS/MIC), IEEE, (Oct. 27, 2013), doi:10.1109/NSSMIC.2013.6829306, pp. 1-3, XP032601397.
Goitein, Michael. 'Organ and Tumor Motion: An Overview.' Seminars in Radiation Oncology. vol. 14, No. 1 (Jan.) 2004: pp. 2-9.
Goldberg, S. Nahum; G. Scott Gazelle, and Peter R. Mueller. 'Thermal Ablation Therapy for Focal Malignancy: A Unified Approach to Underlying Principles, Technigues, and Diagnostic Imaging Guidance.' Amer. J. of Roentgenology, vol. 174, Feb. 2000 pp. 323-331 XP002431995.
Green et al. 'Split cylindrical gradient coil for combined PET-MR system.' Proc. Intl. Soc. Mag. Reson. Med. 16 (2008):352.
Haacke, Mark E. et al. 'Constrained reconstruction: A superresolution, optimal signal-to-noise alternative to the Fourier transform in magnetic resonance imaging.' Medical Physics, AIP, Melville, NY, US, vol. 16, No. 3, May 1, 1989 (May 1, 1989), pp. 388-397, XP000034068, ISSN: 0094-2405, DDI: 10.1118/1.596427.

Hajdok, George. 'An Investigation of Megavoltage Computed Tomography Using a Radioactive Cobalt-60 Gamma Ray Source for Radiation Therapy Treatment Verification.' Thesis. May 2002. 150 pages.
Hernando, D. et al. 'Interventional MRI with sparse sampling: an application of compressed sensing.' Proceedings of International Society for Magnetic Resonance in Medicine.16 (2008):p. 1482.
International Search Report issued by the European Patent Office in International Application No. PCT/US2014/023556 dated Jul. 18, 2014. 6 pages.
International Search Report of the International Searching Authority issued in International Application No. PCT/US2014/028792, dated Jul. 2, 2014. 3 pages.
Irarrazabal, Pablo, and Dwight G. Nishimura. 'Fast Three Dimensional Magnetic Resonance Imaging.' Magnetic Resonance in Medicine, vol. 33, No. 5, 1995, pp. 656-662.
Jaffray, David A., et al. 'Flat-Panel Cone Beam Computed Tomography for Image-Guided Radiation Therapy' Int. J. Radiation Oncology Biol. Phys., vol. 53, No. 5, pp. 1337-1349, Apr. 3, 2002, Elsevier Science Inc., USA.
Jan J. W. Lagendijk et al.; "MR Guidance in Radiotherapy", Physics in Medicine and Biology, Institute of Physics Publishing, Bristol GB, vol. 59, No. 21, Oct. 16, 2014, pp. R349-R369, XP020272054, ISSN: 0031-9155.
Jursinic, Paul et al. 'Characteristics of secondary electrons produced by 6, 10 and 24 MV x-ray beams' Phys. Med. Biol. 41 (1996) 1499-1509, United Kingdom.
Khan, Faiz M., 'The Physics of Radiation Therapy (second edition)', Lippincott Williams & Wilkins. Chapter 13. 1985. pp. 323-332.
Lagendijk et al, 'MRI/linac integration', Radiotherapy and Oncology, Elsevier, Ireland, (Nov. 26, 2007), vol. 86, No. 1, doi:10.1016/J.RADONC.2007.10.034, ISSN 0167-8140, pp. 25-29, XP022423061.
Lagendijk JJ W et al.: "MRI Guided Radiotherapy: A MRI based linear Accelerator", Radiotherapy and Oncology, vol. 56, No. 01, Sep. 21, 2000 (Sep. 21, 2000), pp. S60-S61.
Langen, K.M. et al. 'Organ Motion and its Management.' Int J. Radiation Oncology Biol. Phys., vol. 50, No. 1, pp. 265-278. 2001. Elsevier Science Inc., USA.
Law, C. , and Glover, G. 'Deconvolving Haemodynamic Response Function in fMRI under high noise by Compressive Sampling.' Proceedings of International Society for Magnetic Resonance in Medicine. 17 (2009):p. 1712. Stanford University, Stanford, CA, United States.
Li, Kang and Kanadae, Takeo. 'Nonnegative Mixed-Norm Preconditioning for Microscopy Image Segmentation.' Information Processing in Medical Imaging. Springer Berlin Heidelberg. vol. 5636. (2009):362-373.
Liang, J. and D. Yan. 'Reducing Uncertainties in Volumetric Image Based Deformable Organ Registration.' Medical Physics, vol. 30, No. 8, 2003, pp. 2116-2122.
Lopez, Mike R. et al. 'Relativistic Magnetron Driven by a Microsecond E-Beam Accelerator with a Ceramic Insulator' IEEE Transactions on Plasma Science vol. 32, No. 3, Jun. 2004. pages 1171-1180.
Lucas et al. 'Simultaneous PET-MR: toward a combined microPET. RTM.-MR system.' Proc. Intl. Soc. Mag. Reson. Med. 15(2007):922.
Lurie, D.J., PhD. 'Free radical imaging' The British Journal of Radiology. 74 (2001). pp. 782-784.
Lustig, et al. 'L1 SPIR-IT: Autocalibrating Parallel Imaging Compressed Sensing.' Electrical Engineering, Stanford University, Stanford, CA, United States. Radiology, Stanford University. Statistics, Stanford University (p. 334).
Lustig, M, et al. 'Faster Imaging with Randomly Perturbed, Undersampled Spirals and |L|_1 Reconstruction.' In: Proceedings of the 13th Annual Meeting of ISMRM, Miami Beach, 2005. (1 page).
Mah et al., "Measurement of intrafractional prostate motion using magnetic resonance imaging," Int. J. Radiation Oncology Boil. Phys. Vo.54, No. 2, pp. 568-575, 2002.
Meyer, et al. "Fast Spiral Coronary Artery Imaging", Magnetic Resonance in Medicine 28, pp. 202-213 (1992).

(56) References Cited

OTHER PUBLICATIONS

Notice of Allowance dated Apr. 17, 2019 for U.S. Appl. No. 15/449,774 (pp. 1-5).
Notice of Allowance dated Apr. 7, 2021 for U.S. Appl. No. 16/598,564 (pp. 1-5).
Notice of Allowance dated Feb. 10, 2021 for U.S. Appl. No. 16/204,838 (pp. 1-7).
Office Action dated Apr. 1, 2021 for U.S. Appl. No. 15/630,890 (pp. 1-19).
Office Action dated Jul. 13, 2020 for U.S. Appl. No. 16/362,094 (pp. 1-11).
Office Action dated Jul. 24, 2020 for U.S. Appl. No. 15/630,890 (pp. 1-10).
Office Action dated Mar. 9, 2020 for U.S. Appl. No. 16/204,838 (pp. 1-13).
Office Action dated Nov. 3, 2020 for U.S. Appl. No. 16/362,094 (pp. 1-10).
Office Action dated Sep. 8, 2020 for U.S. Appl. No. 16/204,838 (pp. 1-17).
Office Action dated Nov. 13, 2020 for U.S. Appl. No. 16/598,564 (pp. 1-9).
Overweg et al. 'System for MRI guided Radiotherapy.' Proc. Intl. Soc. Mag. Reson. Med. 17(2009):594.
PCT App. No. PCT/US2010/039036; International Search Report dated Aug. 11, 2010; (pp. 1-2).
PCT App. No. PCT/US2010/042156; International Search Report and Written Opinion dated Sep. 10, 2010 ; 15 pages.
PCT App. No. PCT/US2017/020015; International Search Report and Written Opinion dated Jul. 26, 2017; 18 pages.
PCT App. No. PCT/US2017/038867; International Search Report and Written Opinion dated Nov. 8, 2017; (pp. 1-12).
Raaijmakers, A.J.E. et al. 'Integrating a MRI scanner with a 6 MV radiotherapy accelerator: dose increase at tissue-air interfaces in a lateral magnetic field due to returning electrons.' Phys. Med. Biol. 50 (2005) pp. 1363-1376.
Raaymakers, B.W. et al. 'Integrating a MRI scanner with a 6 MV radiotherapy accelerator: dose deposition in a transverse magnetic field', Phys. Med. Biol. 49 (2004) 4109-4118.
Reddy, B. Srinivasa, and B. N. Chatterji. 'An FFT-Based Technique for Translation, Rotation, and Scale-Invariant Image Registration.' IEEE Transactions on Image Processing, vol. 5, No. 8, Aug. 1996, pp. 1266-1271.
Riek, et al. "Flow Compensation in MRI Using a Phase-Corrected Real Reconstruction", Magnetic Resonance in Medicine 30, pp. 724-731, 1993.
Roullot Elodie et al. 'Regularized reconstruction of 3D high-resolution magnetic resonance images from acquisitions of anisotropically degraded resolutions.' Pattern Recognition, 2000. Proceedings. 15th International Conference on Sep. 3-7, 2000; [Proceedings of the International Conference on Pattern Recognition. (ICPR)], Los Alamitos, CA, USA,IEEE Comput. Soc, US, vol. 3, Sep. 3, 2000 (Sep. 3, 2000), pp. 346-349.
Schreiner, John; Kerr, Andrew; Salomons, Greg; Dyck, Christine, and Hajdok, George, 'The Potential for Image Guided Radiation Therapy with Cobalt-60 Tomotherapy', MICCAI 2003, LNCS 2879, pp. 449-456, 2003.

Schreiner, L. John, et al. 'The role of Cobalt-60 in modern radiation therapy: Dose delivery and image guidance'. Journal of Medical Physics, vol. 34, No. 3, 2009, 133-136.
Sempau, Josep et al. 'DPM, a fast, accurate Monte Carlo code optimized for photon and electron radiotherapy treatment planning dose calculations.' Phys. Med. Biol. 45 (2000) pp. 2263-2291, Received Feb. 29, 2000. Printed in the UK.
Sherouse, George W. et al. 'Virtual Simulation in the Clinical Setting: Some Practical Considerations', Int. J. Radiation Oncology Biol. Phys. vol. 19, pp. 1059-1065, Apr. 26, 1990, Pergamon Press, USA.
Shvartsman et al. 'Gradient Coil Induced Eddy Current Computation Using the Boundary Elements Method.' Proc. Intl. Soc. Mag. Reson. Med. 17(2009):3055.
St. Aubin et al,, 'Magnetic decoupling on the linac in a low field biplanar linac-MR system', Med. Phys, 37 (9), Sep. 2010, pp. 4755-4761.
Tamada and Kose. 'Two-Dimensional Compressed Sensing Using the Cross-sampling Approach for Low-Field MRI Systems.' IEEE Transactions on Medical Imaging. vol. 33, No. 9. Sep. 2014. pp. 1905-1912.
Tokuda, Junichi; Morikawa, Shigehiro; Dohi, Takeyoshi; Hata, Nobuhiko; Motion Tracking in MR-Guided Liver Therapy by Using Navigator Echoes and Projection Profile Matching, 2004. vol. 11. No. 1. pp. 111-120.
Trzasko et al. 'Highly Undersampled Magnetic Resonance Image Reconstruction via Homotopic L0—Minimization' IEEE Transactions on Medical Imaging. vol 28. No. 1. Jan. 31, 2009, pp. 106-121.
Warrington, Jim et al. 'Cobalt 60 Teletherapy for Cancer: A Revived Treatment Modality for the 21st Century', 2002 The Institution of Electrical Engineers, pp. 19-1-19/19.
Wazer, David E. et al. 'Principles and Practice of Radiation Oncology (fifth edition).', Wolters Kluwer/Lippincott Williams & Wilkins. 2008. 2 pages.
Weaver, John B.; "Simultaneous Multislice Acquisition of MR Images", Magnetic Resonance in Medicine, John Wiley & Sons, Inc., vol. 8, No. 3, Nov. 1, 1988, pp. 275-284, XP000003030, ISSN: 0740-3194.
Webb, S. 'The physical basis of IMRT and inverse planning' The British Journal of Radiology, 76 (2003), 678-689, 2003 The British Institute of Radiology.
Webb, Steve, 'Intensity-modulated radiation therapy using only jaws and a mask: II. A simplified concept of relocatable single-bixel attenuators', published May 22, 2002, Institute of Physics Publishing, Physics in Medicine and Biology, Phys. Med. Biol. 47 (2002) 1869-1879.
Yang, Junfeng, et. al. 'A Fast TVL1-L2 Minimization Algorithm for Signal Reconstruction from Radial Fourier Data.' Technical Report, TR08-27, CAAM, Rice University Houston, TX, 2008. pp. 1-10.
Zaitsev M et al.: "Shared k-space Echo Planar Imaging with Keyhole," Magnetic Resonance in Medicine, John Wiley & Sons, Inc. US, vol. 45, Jan. 1, 2001, pp. 109-117, XP002311925, ISSN: 0740-3194.
Zitova B et al., 'Image Registration Methods: a Survey', Image and Vision Computing, Elsevier, Guildford, GB, (Oct. 1, 2003), vol. 21, No. 11, doi:10.1016/S0262-8856(03)00137-9, ISSN 0262-8856, pp. 977-1000, XP001189327.

* cited by examiner

SYSTEMS AND METHODS FOR LINEAR ACCELERATOR RADIOTHERAPY WITH MAGNETIC RESONANCE IMAGING

RELATED APPLICATION(S)

This application is a continuation of and claims priority to and the benefit of U.S. application Ser. No. 16/598,564 filed Oct. 10, 2019, titled "Systems And Methods For Linear Accelerator Radiotherapy With Magnetic Resonance Imaging," which is a continuation of U.S. application Ser. No. 15/268,366 filed Sep. 16, 2016, titled "Systems And Methods For Linear Accelerator Radiotherapy With Magnetic Resonance Imaging," which is a continuation of U.S. application Ser. No. 13/841,478 filed Mar. 15, 2013, titled "Systems And Methods For Linear Accelerator Radiotherapy With Magnetic Resonance Imaging," the disclosures of each are hereby incorporated by reference.

TECHNICAL FIELD

The present disclosure relates to systems and methods for the delivery of linear accelerator radiotherapy in conjunction with magnetic resonance imaging.

BACKGROUND

It is desirable to combine radiation therapy with repetitive real-time imaging using a magnetic resonance imaging system (MRI) in order to better locate and treat therapy targets while sparing nearby healthy tissue. While MRIs and radiation treatment systems such as linear accelerators (linacs) have operated separately from one another for quite some time, combining the two technologies presents many significant technological challenges. Such challenges include the magnetic fields and eddy currents generated in ferromagnetic and conductive radiotherapy equipment through the MRI's main magnet and gradient coils, both of which can destroy an MRI's ability to provide quality images. In addition, an MRI's main magnetic field can interfere with many of the components of a linear accelerator, and the high-power radiofrequency (RF) generated by linac components can likewise destroy the imaging capabilities of the MRI.

SUMMARY

Disclosed herein are systems and methods for combining radiotherapy with magnetic resonance imaging. One embodiment of a disclosed system may include a magnetic resonance imaging system, a gantry, two or more shielding containers attached to the gantry, at least two of the two or more shielding containers containing components of a linear accelerator, and at least one radio frequency waveguide connecting components contained in at least two of the two or more shielding containers.

In another embodiment, the at least one radio-frequency waveguide is oriented to be substantially perpendicular to the magnetic field lines of a main magnet of the magnetic resonance imaging system and/or may include a magnetic shield.

In a further embodiment the two or more shielding containers are spaced substantially equidistant from one another around the circumference of the gantry.

In yet another embodiment, the system may include at least one shielding container that does not contain components of a linear accelerator.

In one embodiment, the system may include multiple radio frequency waveguides, the radio frequency waveguides extending substantially around the entire circumference of the gantry. In some cases, at least one of the radio frequency waveguides will not transmit radiofrequency waves.

In certain embodiments, the system may include three shielding containers adapted to contain RF power source components in a first shielding container, circulator and AFC components in a second shielding container, and linear accelerator components in a third shielding container.

In yet another embodiment, the at least one radio frequency waveguide includes RF shielding. The RF shielding may be an RF absorbing material, an RF reflecting material, or multiple layers of RF reflecting and absorbing materials. And may include carbon fiber, silicon carbide, copper, aluminum, or copper or aluminum alloys or oxides.

In some embodiments, the RF shielding may include water cooling or air cooling.

Embodiments of the disclosure may also include a method of providing a magnetic resonance imaging system, providing a gantry, affixing two or more shielding containers to the gantry, placing components of a linear accelerator into at least two of the two or more shielding containers, and connecting components contained in at least two of the two or more shielding containers with at least one radio frequency waveguide.

In some embodiments of the method, the at least one radio-frequency waveguide may be oriented to be substantially perpendicular to the magnetic field lines of a main magnet of the magnetic resonance imaging system. In other embodiments, the at least one radiofrequency waveguide may include a magnetic shield.

In other embodiments of the method, multiple radio frequency waveguides may be included, extending substantially around the entire circumference of the gantry. In some embodiments, the at least one radio frequency waveguide may include RF shielding, which may be an RF absorbing material, an RF reflecting material, or multiple layers of RF reflecting and absorbing materials and may include air or water cooling.

These and other features, aspects, and advantages of the present disclosure will become better understood with reference to the following description and claims.

BRIEF DESCRIPTION OF DRAWINGS

Features, aspects, and implementations of the disclosure are described in conjunction with the attached drawings, in which.

DETAILED DESCRIPTION

Figure 1:
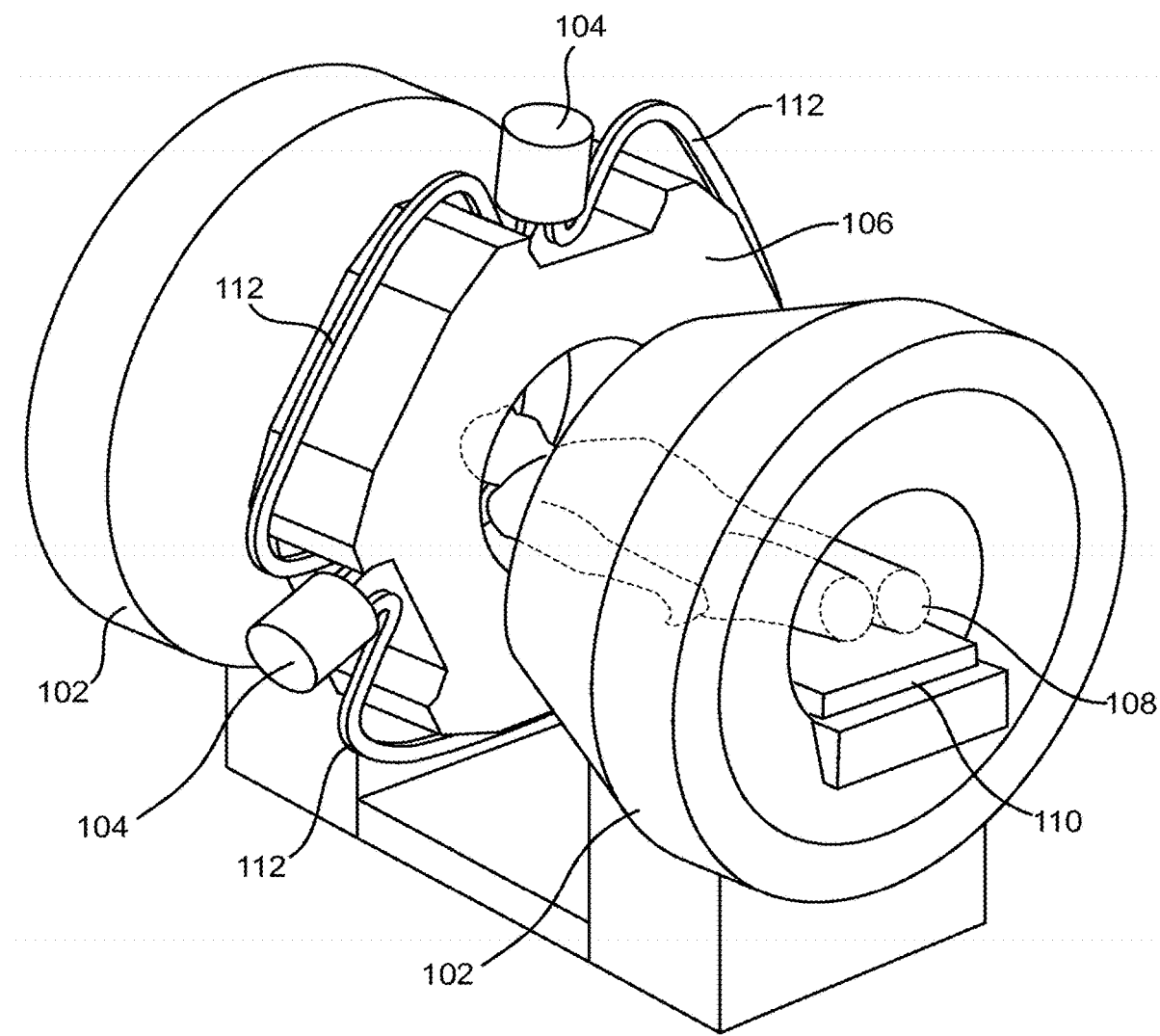
FIG. 1 is a simplified diagram illustrating aspects of a radiation therapy device operating in conjunction with a magnetic resonance imaging system consistent with implementations of the current subject matter.
Figure 2:
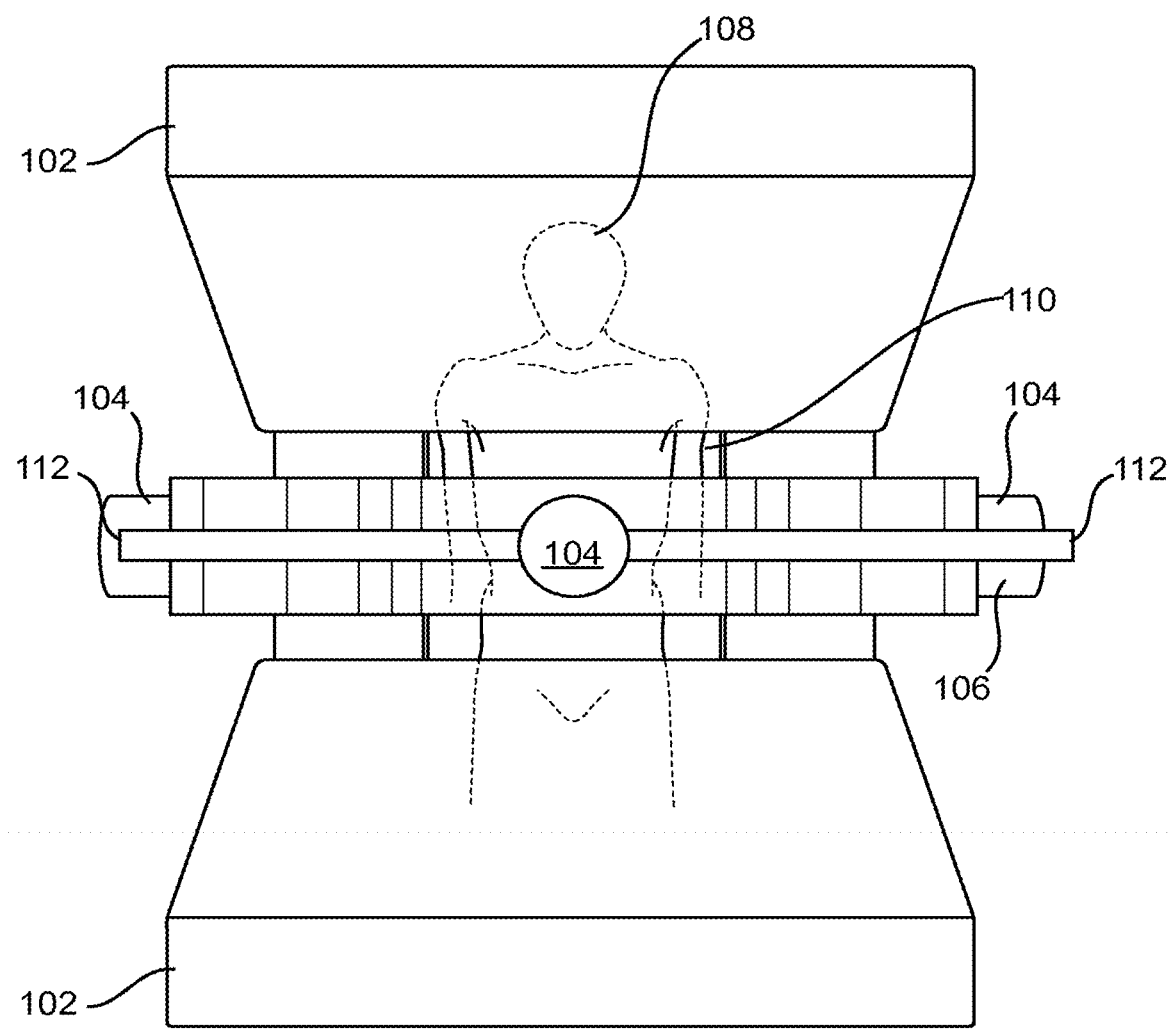
FIG. 2 is a top view of the device depicted in FIG. 1.

Disclosed herein are systems and methods for combining radiotherapy with magnetic resonance imaging. FIG. 1 is a simplified schematic view of an example radiation therapy system including shield containers 104 mounted on a gantry 106, which can rotate to different positions to enable radiation delivery from different angles. The exemplary system depicted in FIG. 1 also includes an MRI 102, which may be used for real-time imaging during radiation therapy and maybe of the split or open type of MRI as shown (as is beneficial so the radiation beam need not be transmitted through the side of an MRI). Radiation therapy devices may be placed inside shield containers 104 and can be used to direct a treatment beam at a target within patient 108 lying on couch 110. Also depicted are waveguides 112, which may be used to connect radiation therapy device components, as explained further below. FIG. 2 depicts a top view of the simplified example system shown in FIG. 1. A similar system is described in U.S. Pat. No. 8,190,233 to Dempsey, titled "System for Delivering Conformal Radiation Therapy while Simultaneously Imaging Soft Tissue," which is hereby incorporated by reference. The system of the present disclosure differs in many respects from that disclosed in Dempsey '233, a primary difference being that the radiation therapy system of the present disclosure specifically includes a linac.

Magnetic resonance imaging is primarily a medical imaging technique most commonly used in radiology to visualize the internal structure and function of the body. MRI is described, for example, by E. MARK HAACKE ET AL., MAGNETIC RESONANCE IMAGING: PHYSICAL PRINCIPLES AND SEQUENCE DESIGN (Wiley-Liss 1999), which is hereby incorporated by reference. The split magnet system illustrated in FIG. 1 includes a pair of main magnets and can also include conventional MRI components not shown, such as a split gradient coil, shim coils and an RF system. The strength of the magnetic field generated by the main magnets can vary, but in an embodiment of the disclosed system the main magnet field strength is 0.35 T.

A linear particle accelerator (also called a linac) is a type of particle accelerator used to accelerate subatomic ions at great speeds. Linacs are described, for example, by C. J. KARZMARK ET AL., MEDICAL ELECTRON ACCELERATORS (McGraw-Hill, Inc., Health Professions Division 1993), which is hereby incorporated by reference. The linac may be designed to accelerate electrons of relatively low energy, in the range of 4 to 6 mega-electron volts (MV) accelerating potential, and have a standing wave guide to keep it compact and, for example, may operate at S-band or X-B and frequencies.

Figure 3:
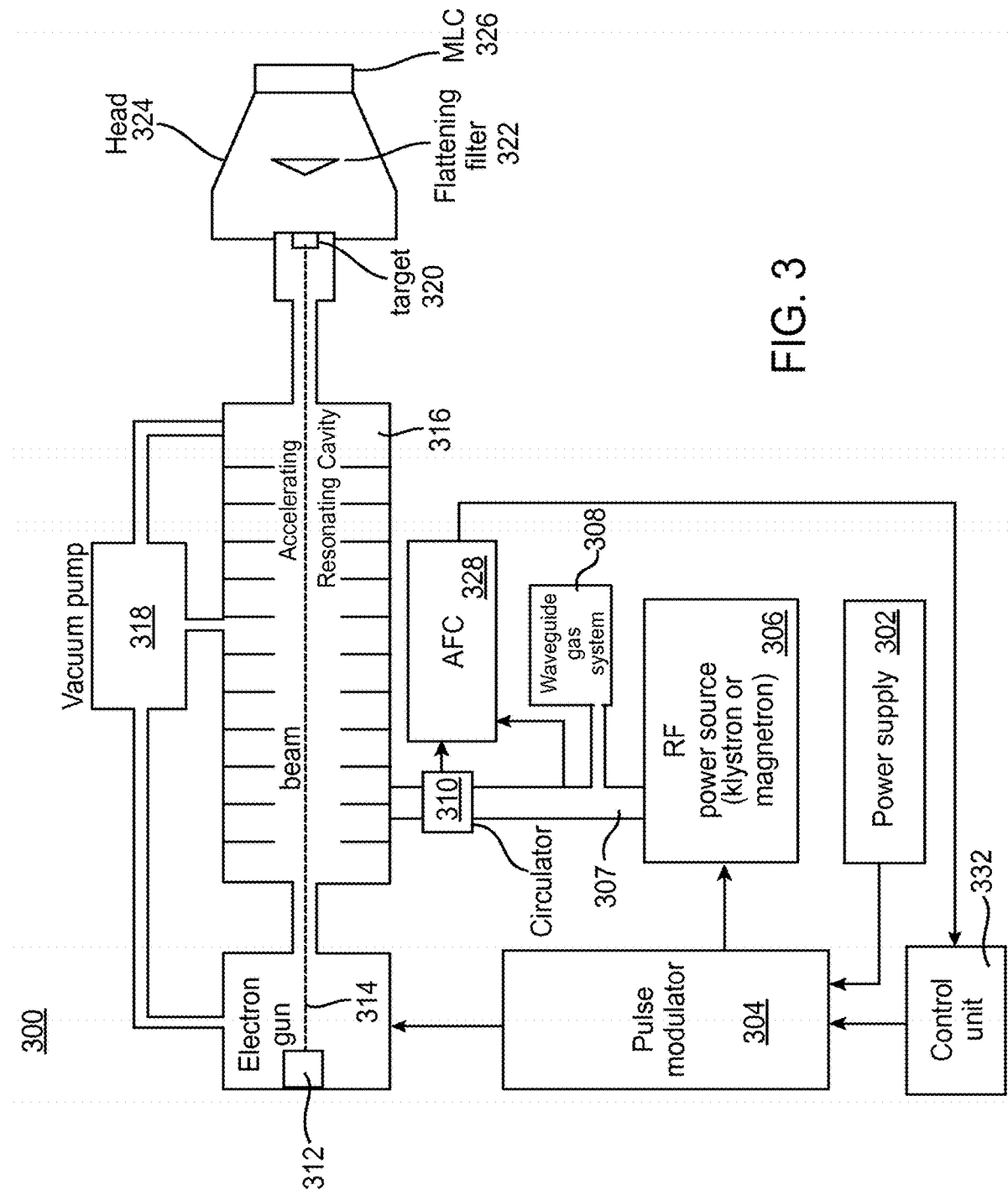
FIG. 3 is a simplified diagram illustrating various components of an exemplary linear accelerator.

FIG. 3 includes a simplified diagram of some of the main components of a linear accelerator 300. The simplified, exemplary linac may include a pulse modulator 304 that may amplify AC power from supply 302, rectify it to DC power, and produce high-voltage DC pulses used to power electron gun 312 and RF power source 306. High-voltage cables electrically connect pulse modulator 304 to the electron gun 312 and RF power source 306. RF power source 306 may be, for example, a magnetron or klystron.

RF power source 306 produces and sends pulses of microwaves, with pulse powers that may be approximately 2.5 mega watts (MW), to accelerating resonating cavity 316 through a waveguide 307. Waveguides 307 may be pressurized by a waveguide gas system 308. Accelerating resonating cavity 316 may be evacuated by vacuum pump 318 and utilize RF pulses from RF power source 306 to accelerate an electron beam 314 generated by electron gun 312. Electron gun 312 creates bursts of electrons, which enter accelerating resonating cavity 316, a resonating cavity excited by RF pulses from the RF power source 306, accelerating an electron beam to near the speed of light.

Electron beam 314 may optionally be aimed at a target 320, commonly made from tungsten, to produce Bremsstrahlung X-rays for x-ray/photon-beam therapy, or the target may be removed for electron-beam therapy. The resulting beam may optionally pass through flattening filter 322 in head 324 prior to entering collimator 326, which may be a multi-leaf collimator as described further below.

The exemplary, simplified linear accelerator 300 depicted in FIG. 3 also includes a circulator 310 and an automatic frequency control system (AFC) 328. The circulator 310 can control the flow of RF waves. For example, it can send energy reflected by the waveguide to an RF dump instead of allowing it back to RF power source 306, which could cause interference or damage. Circulator 310 may also communicate reflected RF waves to AFC 328, which may monitor the reflected waves to determine whether the resonant frequency of accelerating resonating cavity 316 has changed, for example, due to heating. AFC 328 may then communicate with control unit 332, or directly with RF power source 306, to adjust the frequency of the RF waves emitted by RF power source 306.

Figure 4:
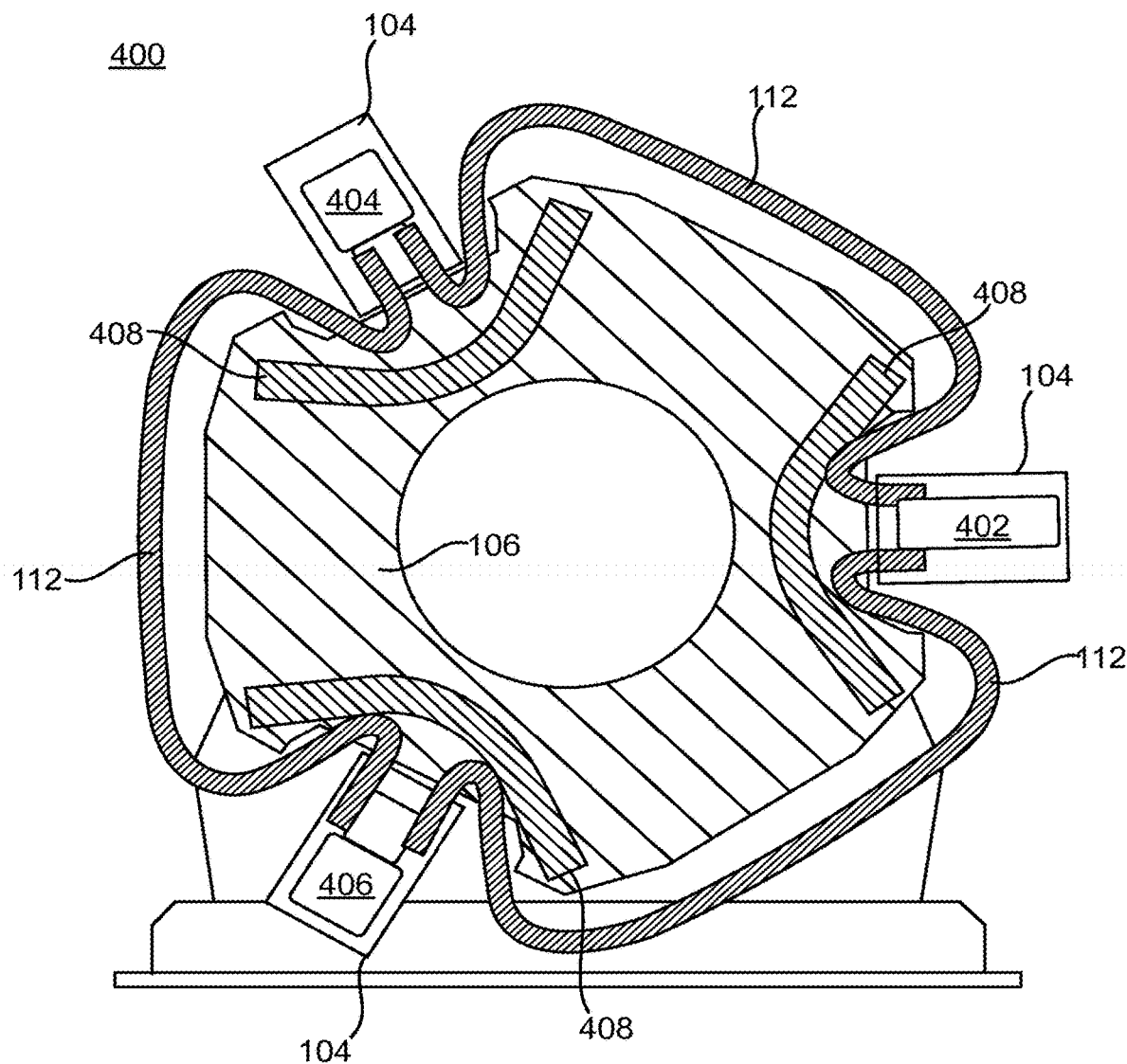
FIG. 4 is a section view of the gantry and associated components of the exemplary device depicted in FIG. 1.

In one embodiment of the disclosure, various components of a linear accelerator, including, but not limited to the linac components illustrated in FIG. 3, may be separated into two or more sets of components that may be attached to gantry 106. FIG. 4 depicts one embodiment of such an arrangement, in which linear accelerator components may be grouped and placed within shield containers 104 around gantry 106. Where the particular groupings of linear accelerator components require as much, RF waveguides 112 can be placed around gantry 106, connecting the various shield containers 104 and the linear accelerator components within. For example, an RF waveguide 112 would be required if RF power source 306 was located within one shield container and the linear accelerator, including electron gun 312, accelerating resonating cavity 316, target 320 and head 324, was in a separate shield container 104 (as shown in FIG. 3, a waveguide 307 is required to transmit the RF energy from the RF power source 306 to the accelerating resonating cavity 316).

This disclosure contemplates any number of potential divisions or groupings of linear accelerator components, and any number of shield containers 104 spaced around gantry 106 to contain such components. In addition, the components to create more than one linear accelerator could be divided and grouped in shield containers 104 around gantry 106 if multiple radiation therapy beams were desired.

In one embodiment, depicted in FIG. 4, there may be three shield containers 104 spaced substantially equidistant from one another around the circumference of gantry 106, with waveguides 112 connecting the shield containers 104 in series. Various groupings of linear accelerator components may be placed in each of shielding containers 104. In an exemplary embodiment, the major components of a linear accelerator may be divided as such: RF power source components 404 may be placed within one shield container 104, circulator and AFC components 406 may be placed in another shield container 104, and linear accelerator components 402 (e.g., electron gun 312, accelerating resonating cavity 316, target 320, head 324 and collimating device 326) may be placed in a third shield container 104. In this embodiment, as well as in other contemplated embodiments, additional linear accelerator components may be distributed amongst the shield containers 104 as is convenient. In addition, certain linear accelerator components may be located off of gantry 106. For example, pulse modulator 304 may be located on the gantry, on the gantry supporting stand, in a separate cabinet outside gantry 106, or possibly outside the RF shielding room of the system. The systems and methods of the disclosure do not require any particular number of shielding containers 104 or any particular groupings or locations of linear accelerator components. The embodiments described herein are merely examples consistent with aspects related to the described subject matter, and any limitations on particular arrangements may only be made in the claims.

One embodiment of the present disclosure may include one or more shielding containers 104 as described herein, or shielding containers 104 consisting merely of materials that mimic the ferromagnetic and conductive aspects of the shielding containers, placed around gantry 106, which do not contain components of a linear accelerator. Such additional shielding containers 104 may be included when shielding containers are not required to hold and/or shield linear accelerator components, but are beneficial in simplifying the ability to shim the overall system for the magnetic field homogeneity necessary for quality imaging by MRI 102. Similarly, embodiments of the disclosure may include one or more waveguides 112, which may merely be made of similar materials that mimic the ferromagnetic and conductive aspects of other waveguides 112, when it is not necessary to transmit RF waves from one shielding container 104 to another (because the container does not include linear accelerator components or because the components within the shielding container do not involve the transmission of RF waves).

Embodiments of shield containers 104 have been described in U.S. patent application Ser. No. 12/837,309 to Shvartsman et al., entitled "Method And Apparatus For Shielding A Linear Accelerator And A Magnetic Resonance Imaging Device From Each Other," which is hereby incorporated by reference. Shield containers 104 can be designed to shield various linear accelerator components from the magnetic field of MRI 102. One example of such a shield includes a shell made of high magnetic permeability material. The shell may be cylindrical in shape with one or both ends of the shell being open. While a cylindrical shape is preferred, the disclosed shield shells can be other shapes. The shell can have a thickness chosen according to characteristics of the shell material and magnetic field being shielded against. The shell may be formed of non-oriented silicon steel, for example a nickel-iron alloy, such as the commercially-available material sold by ThyssenKrupp Steel under the trade name 530-50 AP and having a thickness of, for example, about 5 mm. Other material options include M19 steel, M45 steel, and Carpenter High Permeability "49" Steel. The outer diameter and length of the shell can vary; in the one embodiment, the outer diameter is about 30 cm and the length is about 70 cm.

In some embodiments, shield container 104 can include multiple shield shells. The multiple shield shells may be concentric/coaxial layers of steel, which can be separated by layers of air or other insulating material. In such embodiments, the inner shell(s) can be of a higher permeability but a lower saturation flux density than the outer shells, as the outer shell has already greatly reduced the magnetic field from the MRI 102. In another embodiment, a current carrying coil may be used inside of the inner shell or outside of an outer shell to cancel the residual field.

Embodiments of shield containers 104 may also contain RF shielding to decrease the leakage of RF energy from linear accelerator components to the surroundings. Such shielding may take the form of additional shells of RF absorbing and/or RF reflecting material, as detailed in application Ser. No. 12/837,309, and further below.

As discussed above, radiofrequency waveguides 112 are structures that can transmit RF wave energy, for example, from RF power source 306 to circulator 310 and accelerating resonating cavity 316. In the embodiments of the disclosure, it is contemplated that at least one waveguide 112 will connect two shield containers 104 containing components of a linear accelerator. In other embodiments, waveguides 112 will connect multiple pairs of shield containers 104. In an exemplary embodiment, waveguides 112 will connect each of the multiple shield containers 104 located on gantry 106, spanning substantially around the entire circumference of gantry 106. As detailed above, such an embodiment may be implemented even if the linear accelerator components contained in each of the shield containers 104 do not need to be connected by a waveguide. This embodiment may be beneficial to facilitate shimming of MRI 102 for optimal magnetic field homogeneity.

In one embodiment, waveguides 112 may extend from RF power source components 404 to circulator and AFC components 406 to linear accelerator components 402, and back to RF power source components 404, as depicted in FIG. 4. If necessary, multiple RF waveguides 112 may extend between shield containers 104. For example, if it was necessary to transmit RF waves in both directions between two shield containers 104 based upon the linear accelerator components contained within. In such an embodiment, the same number of waveguides would preferably be placed between each pair of shield containers 104 so that substantial symmetry would exist around the entire circumference of gantry 106.

In one embodiment, waveguides 112 may be made from copper. In other embodiments waveguides 112 may be formed from multiple materials, such as, a non-ferromagnetic metal coated on the interior with copper, silver, gold or another conductive metal. In an exemplary embodiment, waveguides 112 may be pressurized by waveguide gas system 308 with an inert gas such as SF-6 to prevent dielectric breakdown and may have the following specifications: Hollow Rectangular Waveguide, EIA: WR284, RCSC: WG10, IEC: R32, S band, Recommended Frequency Band (GHz): 2.60-3.95, Lower Cutoff Frequency GHz 2.078, Higher Cutoff Frequency GHz 4.156, Inner Wave Guide Dimensions (Inches): 2.840×1.340, with wall thickness WG10: 0.08 inches. Waveguides 112 should also be designed within bending radii restrictions, as is known in the art.

In embodiments where waveguides 112 are not required to transmit RF waves, they may merely be made of materials that mimic the ferromagnetic and conductive qualities of the other waveguides 112.

In one embodiment, waveguides 112 may be magnetically shielded, utilizing, for example, the concepts, materials and designs discussed above with respect to shielding containers 104. Shielding concepts and designs that may also be used are disclosed in U.S. patent application Ser. No. 13/801,680 to Shvartsman et al. entitled "Systems And Methods For Radiotherapy With Magnetic Resonance Imaging," which is incorporated herein by reference.

Figure 5:
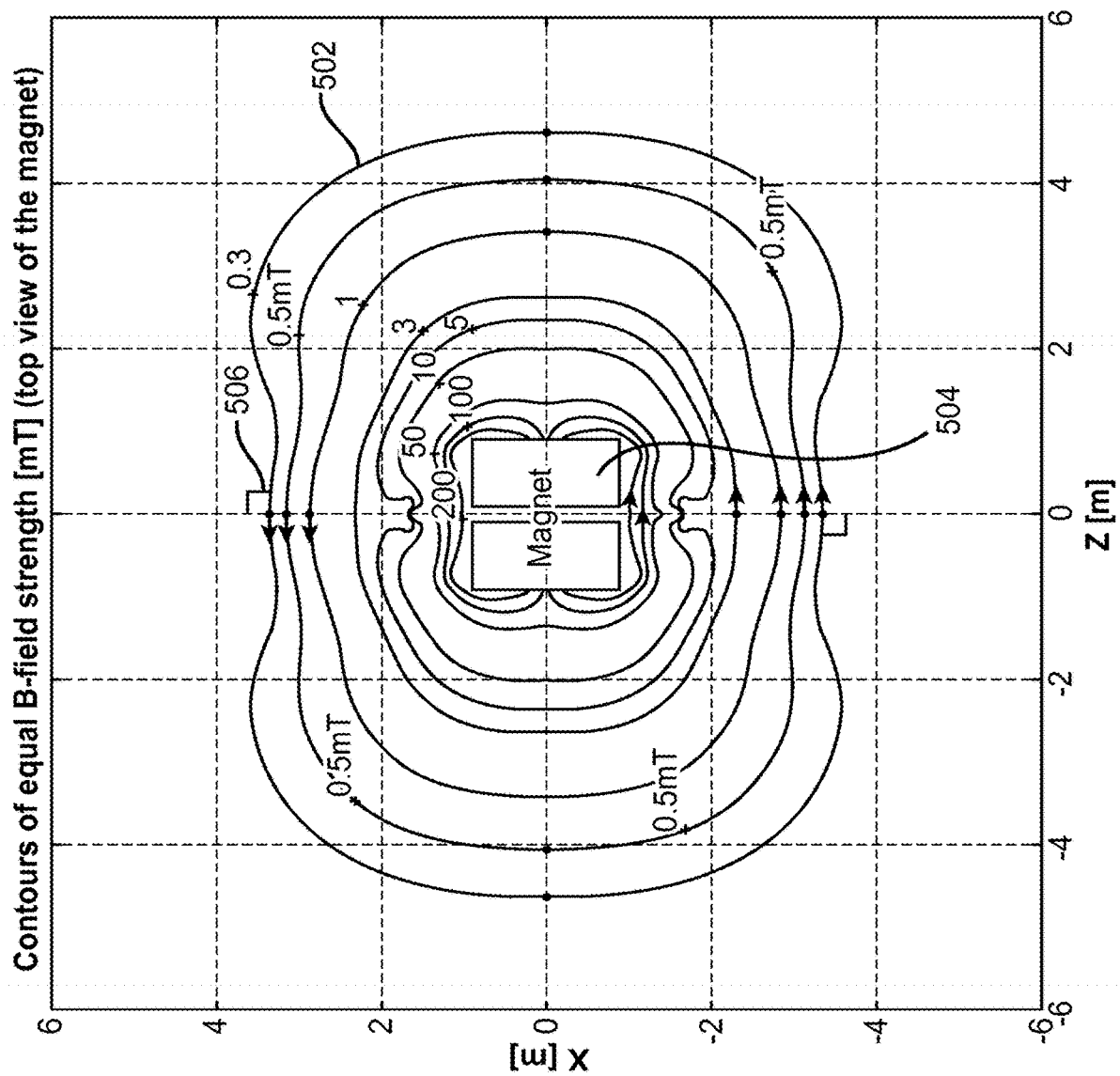
FIG. 5 illustrates a map of magnetic field strength around an exemplary MRI, consistent with implementations of the current subject matter.

In an exemplary embodiment, waveguides 112 do not require magnetic shielding, but instead are oriented to be substantially perpendicular to the main MRI magnet's field lines. FIG. 5 shows an exemplary map of contours 502 of magnetic field strength magnitude for a split MRI 102 having a 0.35 T main magnet. FIG. 5 depicts a top view of an exemplary main magnet 504 as is shown in FIG. 2 also, as magnet halves 102. Right angle indicator 506 in the contour map of FIG. 5 shows that the magnetic field lines for MRI 102 at the preferable location of waveguides 112, as also shown in FIG. 2, will result in the waveguides 112 being substantially perpendicular to the magnetic field lines.

The systems and methods of the present disclosure also include numerous types and placement of radiofrequency shielding and absorbing materials. As discussed above, a linear accelerator's RF power source 306 and electron gun 312 involve the generation of significant radiofrequency energy. Such energy is also transmitted throughout the system via waveguides and within additional linear accelerator components such as a circulator 310 or an AFC 328. Embodiments of radiofrequency shielding disclosed herein control the dispersion and transmission of such RF energy, so as to limit the negative effects on the MRI's ability to acquire quality images resulting from eddy currents or interference with the MRI's radio frequency coils.

As noted above, one embodiment of the disclosure involves the inclusion of RF shielding as part of shield containers 104 in the form of, for example, one or more shells of RF reflective materials such as copper or aluminum, and/or RF absorbing materials such as carbon fiber or Silicon Carbide (SiC). Embodiments may include any number of layers. In some embodiments, the layers of shells can be made of combinations of different materials or of the same material. For example, in some embodiments, the shield shell layers can include alternating layers formed of RF absorbing material and RF reflecting material. In such embodiments, it is desirable to provide an air gap between the layers of shield shells.

When shield containers 104 include linear accelerator components involving the substantial generation of RF energy, the containers 104 may also optionally include RF shielding that covers the top and the bottom of an open cylindrically shaped shield. When shield container 104 contains the linear accelerator itself, the treatment beam will thus pass through the RF shielding. In such a case, the RF shield material is preferably uniform and minimally attenuating to the radiotherapy beam.

In addition to the inclusion of RF shielding in conjunction with shield containers 104, certain embodiments of the disclosure will provide additional RF shielding, for example, around the waveguides 112. The amount of RF energy leakage from the waveguides 112 is likely to be small, and will not necessarily require shielding, however, RF shielding is preferably included at any points where leakage is more likely, such as at flanges, connection points for the waveguides, RF sinks, couplers, etc.

Shielding material may include RF absorbing material such as carbon fiber or silicon carbide (SIC) and/or RF reflecting material such as copper or aluminum. In some embodiments it may be advantageous to provide a number of alternating layers of RF reflecting material and RF absorbing material.

Additionally, such RF absorbing/shielding material can be used to line the interior surface of the room in which the system of the current disclosure is placed. The room walls, ceiling and floor could be lined with meshed or chopped carbon fiber, carbon fiber wallpaper, carbon fiber panels, carbon fiber paint, etc. Furthermore, RF absorbing/shielding material may be placed on the outer surfaces of MRI 102, on gantry 106, and on any linear accelerator components or other components not placed on gantry 106 or MRI 102 (for example, if pulse modulator 304 is not located on the gantry).

The RF shielding materials disclosed herein may be flexible and wrapped around the various components, or may be molded to fit the shape of the components.

Cooling can be provided as needed to the RF shielding/absorbing materials. A variety of known cooling methods can be used. The cooling system may include, for example, fluid-carrying conduit for circulating a fluid in the vicinity of the shielding/absorbing materials. Also, air-cooling can be provided by incorporating a system for moving air across the surfaces of the RF shielding/absorbing materials.

FIG. 4 also depicts collimating devices 408 attached to gantry 106 and associated with each of the shield containers 104. Collimating devices 408 may, for example, be multi-leaf collimators (MLCs), which typically have two banks of opposing pairs of leaves that move independently and can open to form apertures of various shapes and sizes. The leaves may be made of tungsten or any suitable material or materials for blocking radiation. MLCs may also employ a tongue and groove arrangement on the long sides and front of the leaves to limit interleaf radiation leakage and can be configured for inter-digitation of the leaves in the closed position. Each leaf of each bank of leaves may be capable of independent motion and may be driven by leaf motors through connecting rods. An MLC control system can control the two opposing banks of leaves to independently position the edge of each leaf to a specified location in order to block a radiation beam and form a field size of a specific shape. The MLC leaves, motors, and other components may be supported by housing that then attaches to gantry 106. The housing may be, for example, made from aluminum.

In one embodiment, there may be only one collimating device 408, associated with the one shield container 104 that contains the linear accelerator components creating the actual treatment beam. The additional devices 408 may simply be additional conductive elements, utilized to reduce the negative imaging effects of eddy currents generated during operation of the MRI's gradient coils. Such devices can be designed as described in U.S. patent application Ser. No. 13/801,680 to Shvartsman et al. entitled "Systems And Methods For Radiotherapy With Magnetic Resonance Imaging," which is incorporated herein by reference. Consistent with the teachings of the incorporated application, embodiments of the system of this disclosure may include, for example, additional conductive elements. In one embodiment, a multi-leaf collimator occupies the space shown as 408 adjacent the shield container 104 containing the linear accelerator, while five additional equally spaced conductor elements are attached around the remaining circumference of gantry 106.

Additional shimming and shielding concepts disclosed in application Ser. Nos. 13/801,680 and 12/837,309 are also applicable to the systems and methods disclosed herein, and are also fully incorporated by reference. For example, additional shimming for magnetic field homogeneity can be provided by permanent magnets, optionally made from Neodymium (NdFeB). The polar orientation of the permanent magnets should be such that they counteract the MRI's main magnetic field and the magnetic field induced in various ferromagnetic materials in the vicinity of MRI 102. The canceling effect of the magnet design's strengths, field orientations, and locations can be determined utilizing modeling software such as FARADAY, available from Integrated Engineering Software, or any other appropriate software such as VectorField, for example, and with further analysis of results potentially being performed in a program such as MATLAB or any other appropriate software such as FORTRAN, for example. As an alternative to permanent magnets, active windings could also be used. Such active shimming concepts are disclosed in U.S. application Ser. No. 13/324,850 to Shvartsman et al. entitled "Active Resistive Shimming For MRI Devices," also incorporated herein by reference.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. Other implementations may be within the scope of the following claims.

What is claimed is:

1. A system for radiotherapy, the system comprising:
a magnetic resonance imaging system configured to generate a main MRI magnetic field along an MRI axis;
a gantry configured to rotate about the MRI axis;
a first component of a linear accelerator attached to the gantry;
a second component of the linear accelerator attached to the gantry at a separate location around the gantry; and
a radio-frequency (RF) waveguide connecting the first component and the second component of the linear accelerator, wherein the RF waveguide is oriented to be substantially perpendicular to the main MRI magnetic field.

2. The system of claim 1, the radio frequency waveguide is made substantially from copper.

3. The system of claim 1, wherein the radio frequency waveguide is formed from a non-ferromagnetic material coated with copper on an interior surface of the radio frequency waveguide.

4. The system of claim 1, wherein the radio frequency waveguide is formed from a non-ferromagnetic material coated with silver on an interior surface of the radio frequency waveguide.

5. The system of claim 1, wherein the radio frequency waveguide is formed from a non-ferromagnetic material coated with gold on an interior surface of the radio frequency waveguide.

6. The system of claim 1, wherein the radio frequency waveguide is formed from a non-ferromagnetic material coated with a conductive metal on an interior surface of the radio frequency waveguide.

7. The system of claim 1, further comprising a third component of the linear accelerator, the third component being a pulse modulator located on the gantry.

8. The system of claim 1, the system further comprising a gantry supporting stand and a third component of the linear accelerator, the third component being a pulse modulator located on the gantry supporting stand.

9. The system of claim 1, the system further comprising a cabinet outside the gantry and a third component of the linear accelerator, the third component being a pulse modulator located in the cabinet.

10. The system of claim 1, the system further comprising:
an RF shielding room containing the magnetic resonance imaging system and the gantry; and
a third component of the linear accelerator, the third component being a pulse modulator located outside the RF shielding room.

11. The system of claim 1, wherein the radio frequency waveguide includes RF shielding.

12. The system of claim 11, wherein the RF shielding comprises at least one of an RF absorbing material, an RF reflecting material, or multiple layers of RF reflecting and absorbing materials.

13. The system of claim 1, further comprising:
a first shielding container mounted on the gantry, the first component of the linear accelerator at least partially within the first shielding container; and
a second shielding container mounted on the gantry at a separate location around the circumference of the gantry from the first shielding container, the second component of the linear accelerator at least partially within the second shielding container.

14. The system of claim 1, further comprising
a first shielding container on the gantry, the first component of the linear accelerator at least partially within the first shielding container; and
a second shielding container on the gantry at a separate location around the gantry from the first shielding container, the second component of the linear accelerator at least partially within the second shielding container,
wherein the radiofrequency waveguide is connecting the first component of the linear accelerator and the second component of the linear accelerator.

15. The system of claim 1, the system further comprising:
a first RF shielding around the first component of the linear accelerator configured to decrease leakage of RF energy from the first component of the linear accelerator to surroundings; and
a second RF shielding around the second component of the linear accelerator configured to decrease leakage of RF energy from the second component of the linear accelerator to the surroundings.

16. The system of claim 15, wherein the first RF shielding or the second RF shielding comprises at least one of: an RF absorbing material, an RF reflecting material, and multiple layers of RF reflecting and absorbing materials.

* * * * *